(12) United States Patent
Plath

(10) Patent No.: US 9,492,308 B2
(45) Date of Patent: Nov. 15, 2016

(54) URINATION ASSISTANCE DEVICE

(71) Applicant: Dave Plath, Schereville, IN (US)

(72) Inventor: Dave Plath, Schereville, IN (US)

( * ) Notice: Subject to any disclaimer, the term of this patent is extended or adjusted under 35 U.S.C. 154(b) by 64 days.

(21) Appl. No.: 13/987,027

(22) Filed: Jun. 26, 2013

(65) Prior Publication Data

US 2015/0000024 A1  Jan. 1, 2015

(51) Int. Cl.
*E03D 13/00* (2006.01)
*A47K 11/00* (2006.01)
*A61F 5/453* (2006.01)
*A61F 5/44* (2006.01)

(52) U.S. Cl.
CPC .............. *A61F 5/453* (2013.01); *A61F 5/4404* (2013.01)

(58) Field of Classification Search
CPC ........... E03D 11/13; A61F 5/453; A61F 5/404
USPC .............................. 4/301, 144.1–144.4, 114.1
See application file for complete search history.

(56) References Cited

U.S. PATENT DOCUMENTS 8,424,125 B2 * 4/2013 Anderson ............................ 4/342
2009/0100587 A1 * 4/2009 Smith ................................ 4/496

* cited by examiner

*Primary Examiner* — Huyen Le
*Assistant Examiner* — Christine Skubinna
(74) *Attorney, Agent, or Firm* — Paul E Schaafsma; NovusIP, LLC

(57) ABSTRACT

A urination assistance device for use with a bowl toilet is provided: A downwardly-extending receptacle collects urine. A stabilizing frame is provided designed to allow the urination assistance device to rest upon a toilet seat or upon the rim of the toilet bowl. The stabilizing frame defines a pair of ends, with each end terminating with a downward oriented elbow. The base member including a downward directed spout in operative communication with the receptacle to discharge any urine collected within the receptacle into the toilet bowl. The spout is in or in near contact with the upper portion of the interior wall of the front of the toilet bowl.

19 Claims, 3 Drawing Sheets

URINATION ASSISTANCE DEVICE

FIELD OF THE INVENTION

The present invention relates to urination assistance devices.

BACKGROUND OF THE INVENTION

When standard-bowl toilets are used by males to urinate while standing, there is inevitably some splashing of urine as the urine falls into the toilet bowl. Even small amounts of urine escaping the bowl cause considerable contamination of the surroundings, resulting in malodorous, unsanitary conditions. The problem is exacerbated when the male is physically handicapped, or is suffering from lost, or deficient, motor control, as such male is much more likely to experience significant problems with directing urine from a standing position into the bowl. Likewise, young males, especially those training to use a standard-bowl toilet as a urinal, may lack sufficiently accurate aim and balance to direct the stream of urine into the toilet bowl, and they may wet the outlet portions of the toilet bowl and seat, and area around the toilet.

Physically handicapped males who are bound to wheelchairs experience additional challenges with using a toilet to urinate. One such challenge is that, in order to use the toilet, they must transfer themselves from the wheelchair onto a toilet seat. However, a wheelchair bound male may not have enough upper body strength, or be otherwise capable, to lift up from the wheelchair and transfer onto a toilet bowl. Such male may require the assistance of others to be transferred. This may especially be the case with males that are older, are heavier, and who may suffer from a myriad of other medical conditions.

Moreover, transferring a person from a wheelchair onto a toilet seat can be time-consuming, which is undesirable when the person must use the toilet within a short period of time; and it can be burdensome, when the person must use the toilet often, such as for example a male suffering from prostate problems. In addition, relying on others to provide assistance with using a toilet can be embarrassing to a wheelchair bound male. Further, bathroom facilities may have to be specifically designed to allow enough room for the transfer of a wheelchair bound male onto a toilet, and special handlebars may have to be installed in various locations around the bathroom facility to provide support. Still further, the toilet seat may also have be specifically designed to provide enough support to a male who does not have the use of his lower extremities to safely use the toilet.

Another medical condition that can cause difficulties in urination is split stream, or splitting of the urinary stream. Split stream occurs when an area of relative narrowing of the urinary canal (urethra). Split stream also can be caused by scarring of the urinary opening, damage to the urethra or by some residual debris in the urinary tube. This may occur anywhere in the urethra from the neck of the bladder to the opening of the urethra at the end of the penis (meatus). Prostate infections or enlargement can also cause one flow to double-up.

Various devices have been suggested in attempting to prevent males from urinating on a floor or a surface of a toilet, and to prevent the urine from splashing outwardly from the toilet bowl during urination. For example, in the use of one type of such devices, an attachment for the toilet acts as a splash guard such that when splashing occurs during urination or when the stream of urine is not directly directed into the toilet opening, the urine hits the guard and runs down the front into the toilet bowl. Various types of splashguards have been proposed, such as shields that wrap around a back portion of the circumference of a toilet bowl.

Nevertheless, such devices experience a number of drawbacks. One of the drawbacks is that these devices are generally ineffective to assist a wheelchair bound male with using a toilet. These devices are generally mounted on the surface of a toilet seat, or otherwise extend upwardly from the toilet seat, preventing a person from sitting on the toilet seat.

Another drawback is that such devices are generally ineffective in preventing spilling and splashing of urine, which may occur in the front portion of the toilet bowl where the male user is standing. This may particularly be the case with younger users, who are more prone to move around while urinating, and who may not be able to accurately direct the stream of urine into the bowl, or who may be unable to produce a strong enough stream of urine.

Another drawback of such devices is that they have relatively large outer surface areas and are generally difficult to clean. Thus, such devices generally must be washed in a large container such as a bathtub, using large amounts of water, and are difficult to store without dripping.

Nor do such devices generally offer an effective training aid for younger males. The presence of a "target" on the back of the toilet may lead young males to aim too high, thereby training them to overshoot the bowl.

Another type of such devices involves the use of an attachment mounted to a toilet bowl. Some of such devices involve the use of a receiver connected to a flexible tubular duct member, which is in turn connected to the toilet fixture, to provide an outlet for the urine collected in the receptacle. In some other devices, a receiver is adapted to be mounted to the underside of a toilet seat, to be raised and lowered with the seat.

However, such devices also experience a number of drawbacks. One of the drawbacks is that these devices are generally not portable, as to allow users to use these devices while traveling. Such devices may not be stored away from the toilet when not in use, further taking away from the aesthetics of the bathroom.

Another drawback is that such devices are difficult to use by younger males and those males who may be confined to a wheelchair. In order for these devices to be operated, the user must lift the seat cover and disengage the receiver, and move it outwardly from the seat. When the user is finished, the receiver must be returned to the storage location. Due to the complexity of use, and location of such devices, young and handicapped users may be unable to reach far enough to disengage the receptacle, making such devices difficult, if not impossible, to operate.

Still further, devices mounted on the underside of a toilet seat may become unsanitary. By the nature of their location, when the seat is lowered, these devices may come in contact with solid waste when the toilet is flushed, requiring that the devices be cleaned even when not in use to prevent the growth of bacteria.

Thus, what would be desirable would be a urination assistance device capable of being used by males who urinate while standing and by those who must urinate while sitting, such as for example, males who are confined to a wheelchair. It would be desirable for the device to require minimal manipulation to accommodate younger users and those who may be confined to a wheelchair. It would also be desirable for the device to be easily adapted for storage. It would further be desirable for the device to be portable to provide urination assistance outside of the user's home, for example, in a travel setting. It would further be desirable for the device to be capable of use with toilets of various sizes, with or without a toilet seat. It would further be desirable for the device to have design features that encourage young males to toilet train and to develop accurate aim while urinating.

SUMMARY OF THE INVENTION

A urination assistance device in accordance with the principles of the present invention is capable of being used by males who urinate while standing and by those who must urinate while sitting, such as for example, males confined to a wheelchair. A urination assistance device in accordance with the principles of the present invention requires minimal manipulation to accommodate males of various heights and those who may be confined to a wheelchair. A urination assistance device in accordance with the principles of the present invention can easily be adapted for storage. A urination assistance device in accordance with the principles of the present invention is portable and can provide urination assistance outside of the user's home, for example, in a travel setting. A urination assistance device in accordance with the principles of the present invention can be used with toilets of various sizes, with or without a toilet seat. A urination assistance device in accordance with the principles of the present invention has design features that encourage young males to toilet train and to develop accurate aim while urinating.

In accordance with the principles of the present invention, a urination assistance device is provided. A downwardly-extending receptacle collects urine. A stabilizing frame is provided designed to allow the urination assistance device to rest upon a toilet seat or upon the rim of the toilet bowl. The stabilizing frame defines a pair of ends, with each end terminating with a downward oriented elbow. The base member including a downward directed spout in operative communication with the receptacle to discharge any urine collected within the receptacle into the toilet bowl. The spout is in or in near contact with the upper portion of the interior wall of the front of the toilet bowl.

This Summary introduces concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description refers to the following accompanying drawings.

DETAILED DESCRIPTION OF THE PREFERRED EMBODIMENTS

Figure 1:
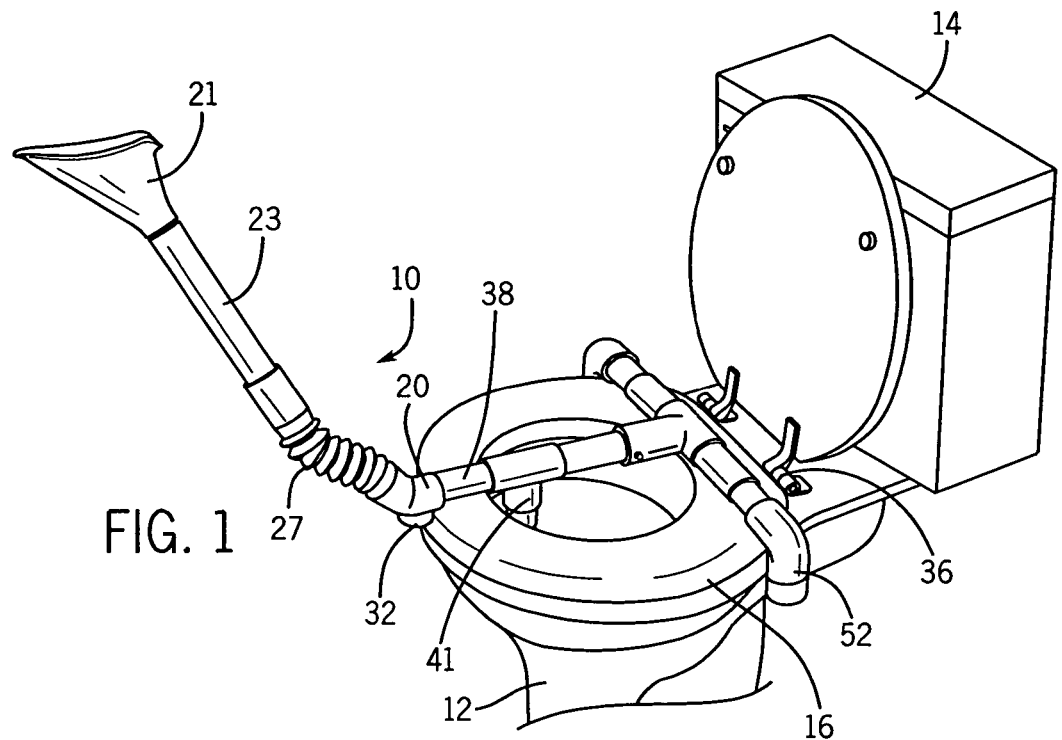
FIG. 1 is a side prospective view of an example urination assistance device in accordance with the principles of the present invention.
Figure 2:
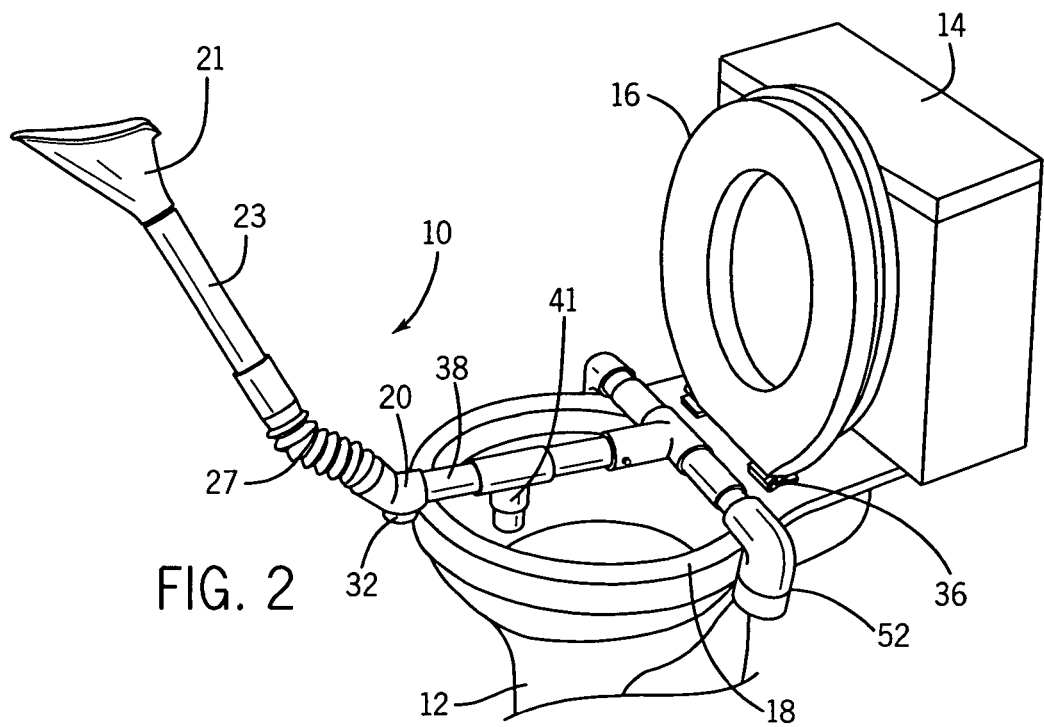
FIG. 2 is a side prospective view of the urination assistance device of FIG. 1 resting upon a toilet bowl rim.
Figure 3:
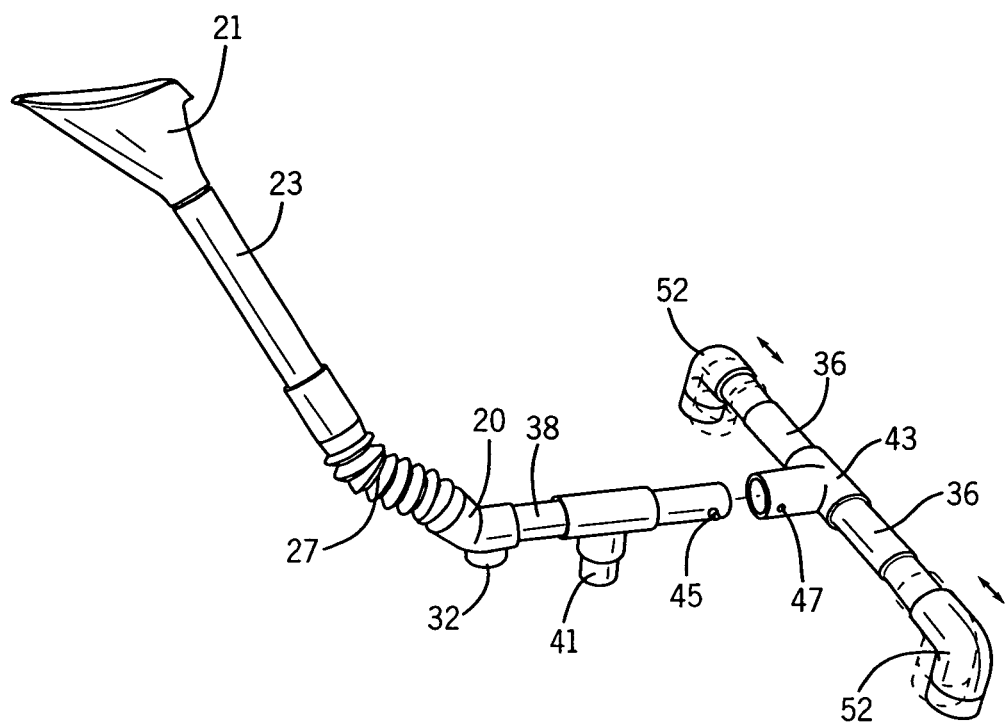
FIG. 3 is a side prospective view of the urination assistance device of FIG. 1, with the cross member detached from the base member.

In accordance with the principles of the present invention, a urination assistance device 10 is provided. Referring to FIGS. 1-3, the urination assistance device 10 is adapted to rest above the bowl 12 of a standard toilet 14. The toilet 14 can be of any conventional type and size, in that the particular toilet does not form a part of the present invention. Also, the toilet can be installed in any setting, such as in a bathroom of a home, hospital or hotel, particularly since the present invention is ideal for travel. As detailed below, the urination assistance device 10 can be utilized above the bowl 12 with the seat 16 in the lower position resting upon the seat 16 (as seen in FIG. 1) or with the seat in the upper position resting on a toilet bowl rim 18 (as seen in FIG. 2).

The urination assistance device includes a receptacle 21. The receptacle 21 is connected to a stabilizing frame 20 at the front edge of the toilet 14. In one embodiment (seen in FIGS. 1-3), an outlet leg 23 extends downwardly and connects the receptacle 21 to the stabilizing frame 20. The stabilizing frame 20 is designed to allow the urination assistance device 10 to rest securely upon the toilet seat 16 or upon the rim 18 of the toilet bowl 12 to help prevent the urination assistance device 10 from moving while in use. The stabilizing frame 20 includes a T-shaped arm connected to the outlet leg 23 (seen in FIGS. 1-3) or to the receptacle 21 (seen in FIG. 4) at the front edge of the toilet 12. The T-shaped arm is comprised of a cross member 36 connected to a base member 38. The base member 38 includes a downward directed spout 41. The cross member 34 defines a pair of ends, with each end terminating with a downward oriented elbow 52.

In more detail, the receptacle 21 is generally funnel-shaped to assist downward movement of the urine within the receptacle 21, and acts as a splash guard to help prevent urine from splashing and spilling around the toilet. When the urine stream is not directed directly at the opening defined in the bottom of the receptacle 21, the urine hits the walls of the receptacle 21 and runs down it unto the opening defined in the bottom of the receptacle 21.

In one embodiment, the lower surface wall of the generally funnel-shaped receptacle 21 extends further away from the opening defined in the bottom of the receptacle 21, to provide a larger surface for catching urine to further help prevent splashing and spilling of the urine; however, the receptacle 21 can be of any appropriate shape or configuration including, but not limited to, circular, oval, elliptical, rectangular or polygonal.

In one embodiment, the receptacle 21 includes an outlet leg 23 connected to a stabilizing frame 20. The stabilizing frame 20 rests upon the toilet seat 16 or the toilet bowl rim 18. The outlet leg 23 extends downwardly toward the toilet bowl 12 to discharge urine collected within the receptacle 21 into the toilet.

In one embodiment, the outer leg 23 comprises a telescopic extendable member that allows the length of the outer leg 23 to be increased or decreased depending on the needs of the user. The outer leg 23 can be telescoped outwardly to accommodate taller users and users who may be positioned farther away with respect to the toilet 14. The outer leg 23 can be telescoped inwardly to accommodate shorter users and users who may be positioned closer with respect to the toilet. Of course, other means for extending the length of the outer leg 23 can be utilized.

In one embodiment, at the lower portion of the outlet leg 21, a flexible, ribbed or corrugated tube portion 27 is provided, made of an appropriate material. The ribbed or corrugated tube 27 is capable of being stretched or bent to allow the user to adjust the angle and position of the receptacle 21. For example, a shorter user, or a user who is bound to a wheelchair, may bend the ribbed or corrugated rube 27 in a downward direction to lower the angle and position of the receptacle 21; a taller user, or a user standing closer to the toilet, may bend the ribbed or corrugated tube 27 in an upward direction to increase the angle and position of the receptacle 21. Herein, the terms ribbed and corrugated shall have the same meaning and will be used interchangeably.

At the terminus of the outlet leg 23 (FIGS. 1-3) or the receptacle 21 (FIG. 4) a downward directed nub 32 is defined. When the urination assistance device 10 is in use, the nub 32 is in or in near contact with the outer wall of the front of the toilet bowl rim 18 (as seen in FIG. 2) or the seat 16 (as seen in FIG. 1). The nub 32 serves as one of the stabilizing components that form the stabilizing frame 20 of the urination assistance device 10. The nub 32 functions as a stop to help prevent the urination assistance device 10 from moving toward the toilet bowl 12. The stabilizing frame 20 further includes a T-shaped arm. The T-shaped arm is comprised of a cross member 36 connected to a base member 38 (best seen in FIG. 3). The T-shaped arm is connected to the outlet leg 23 through the base member 38, at the outer wall of the front of the toilet bowl 12.

The base member 38 includes a downward directed spout 41. Urine collected within the receptacle 21 flows downwardly through the base member 38 to the spout 41 to discharge the urine to the toilet bowl 12. On the opposite side of the location of the spout 41, the base member 38 defines a barrier to help prevent urine from continuing to flow through the base member 38 past the spout 41. In one embodiment, the portion of the base member 38 past the spout 41 is solid.

The spout 41 also serves as one of the components of the stabilizing frame 20 (best seen in FIGS. 1 and 2). When the urination assistance device 10 is in use and rests upon the toilet seat 16 or toilet bowl rim 18, the spout 41 is in or in near contact with the upper portion of the interior wall of the front of the toilet bowl 12. Thus, the nub 32 and the spout 41 are spaced sufficiently apart to allow a toilet seat 16 and rim 18 of a conventional width to fit between the nub 32 and the spout 41. The nub 32 and the spout 41 thus help keep the urination assistance device 10 generally in place to help prevent the urination assistance device 10 from moving away and toward the toilet bowl 12.

Referring back to FIG. 3, in one embodiment the base member 38 is removably attached to the cross member 36. In one embodiment, a t-shaped sleeve connector 43 is provided attached to the cross member 36, which t-shaped sleeve connector 43 slides over the base member 38. Of course, other connectors can be utilized such as, for example, the t-shaped sleeve connector 43 can be provided attached to the base member 38 wherein the t-shaped sleeve connector 43 slides over the cross member 36.

In one embodiment, the base member 38 can be secured to the cross member 36 by a snap connection system. One or two axially spaced spring-loaded male members 45 (only one seen in FIG. 3) are provided on each side of the base member 38. A pair of cooperating apertures 47 (only one seen in FIG. 3) are defined in the cross member 36. During insertion, the spring-loaded male members 45 are pushed inwardly, snapping outwardly when aligned with the cooperating apertures 47 to secure the base member 38 and the cross member 36. To remove, the spring-loaded male members 45 are again pushed inwardly, thus releasing base member 38 from the cross member 36. Of course, other connectors can be utilized such as for example a slip connector.

The cross member 36 defines a pair of ends extending away toward opposite edges of the toilet bowl 12 in a direction substantially perpendicular to the direction of the base member 38. Each end terminates with a downward oriented elbow 52. Each elbow 52 functions as a stop to help prevent the urination assistance device 10 from lateral movement. In one embodiment, to accommodate toilet bowls of various sizes, each end comprises a telescopic extendable means to allow the length of each end to be increased or decreased depending on the size of the toilet 14. When the urination assistance device 10 is in use, the elbows 52 are in or in near contact with the outer walls of the sides of the bowl 12. The elbows 52 serve as one of the components that form a stabilizing frame 20 of the urination assistance device 10, functioning to help prevent the urination assistance device 10 from lateral movement. Thus, in FIG. 1 the elbows 52 are seen telescoped outwardly to accommodate the size of the seat 16; in FIG. 2 the elbows 52 are seen telescoped inwardly to accommodate the size of the bowl 12.

In one embodiment, each elbow 52 can be weighted to provide further stability and to help prevent the urination assistance device 10 from becoming unstable and from falling forward. The weighing of each elbow 52 can accomplished by any means, including but not limited to inserting a weighted material into each elbow 52, or manufacturing each elbow 52 with a material heavier than the remaining components of the urination assistance device 10.

In one embodiment, the base member 38 extends past the widest portion of the toilet bowl 12, so that when extended to the desired length, the length of the cross member 36 is less than the diameter of the toilet bowl 12. The elbows 52 of each end of the cross member 36 come in or in near contact with the toilet bowl 12 past the widest section of the toilet bowl 12. Because the movement of the urination assistance device is obstructed by the shorter length of the cross member 36 with respect to the diameter of the toilet bowl 12, this helps provide additional support to the urination assistance device 10, to help prevent the urination assistance device 10 from moving away from the toilet 14.

Thus, in one aspect, the urination assistance device can be used by males urinating in a standing position and those males who are required to sit while urinating, such as males who are confined to a wheelchair. In another aspect, the urination assistance device generally helps prevent urine from splashing and spilling around the toilet. In another aspect, the urination assistance device is portable, allowing the user to use it virtually any setting when a toilet is present, such as for example when traveling.

By providing a stable urine receptacle that can easily be adjusted by the user to the desired angle and height, spilling and splashing of urine around the toilet is lessened. In addition, by providing a stable urine receptacle that extends away from the toilet and can easily be adjusted to accommodate wheelchair bound users, assistance of third persons is not required. This reduces the embarrassment some wheelchair bound users may experience stemming from having third persons present in the bathroom when they urinate, and from having to be touched by those persons to be lifted from the wheelchair onto the toilet seat.

While not specifically so limited, the example urination assistance device 10 described in connection with FIGS. 1-3 is generally applicable to use by an adult, such as a wheelchair bound male. As previously mentioned, a urination assistance device in accordance with the principles of the present invention can be utilized to encourage young males to toilet train and to develop accurate aim while urinating.

Figure 4:
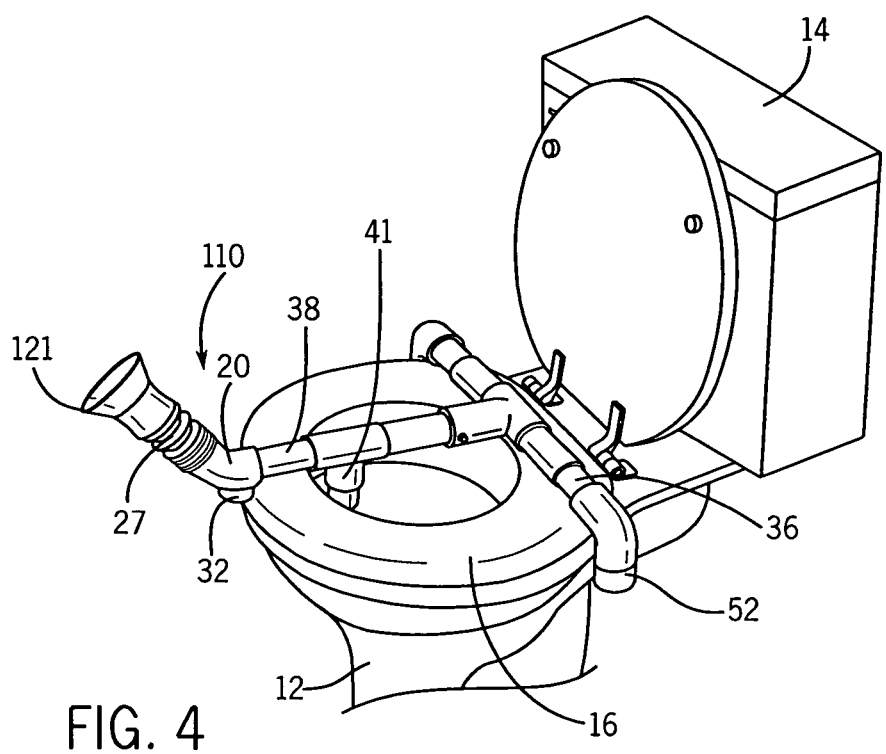
FIG. 4 is side prospective view of a second example urination assistance device in accordance with the principles of the present invention.

Referring now to FIG. 4, a second sample urination assistance device 110 in accordance with the principles of the present invention is seen. While not specifically so limited, the example urination assistance device 110 described in connection with FIG. 4 is generally applicable to be utilized to encourage young males to toilet train and to develop accurate aim while urinating.

Thus, in FIG. 4, like elements have the same reference numerals. The urination assistance device 110 includes a stabilizing frame 20 resting upon a toilet seat 16 (or a toilet bowl rim 18). A ribbed or corrugated tube portion 27 is provided made of flexible material. A downward directed nub 32 is in or in near contact with the outer wall of the front of the seat 16 (or bowl rim 18). The base member 38 includes a downward directed spout 41. The cross member 36 includes a downward oriented elbow 52.

The urination assistance device 110 also includes a receptacle 121 for collecting urine. In contrast to the receptacle 21 of the previous example, the receptacle 121 is circular to encourage young males to develop accurate aim while urinating. In addition, as a result of the height of a young male toilet training, the receptacle 121 can be directly connected the ribbed or corrugated tube portion 27 (as seen in FIG. 4) or to a shortened outlet leg 23.

Thus, the urination assistance 110 device of FIG. 4 omits the outlet leg 23 to better suit the needs of a young male who is toilet training. In one aspect, the urination assistance device can be utilized to encourage young males to toilet train and to develop accurate aim while urinating, by providing a more specific target than the embodiment of FIGS. 1-3. In another aspect, the urination assistance device is portable allowing the user to use it virtually in any setting when a toilet is present, such as for example when the young male is traveling with his legal guardians.

It should be understood that various changes and modifications to preferred embodiments described herein would be apparent to those skilled in the art. Such changes and modifications can be made without departing from the spirit and scope of the present invention and without demising its attendant advantages. It is therefore intended that such changes and modifications be covered by the appended claims.

What is claimed is:

1. A urination assistance device for use with a bowl toilet comprising:
   a receptacle for collecting urine, the receptacle extending downwardly;
   a stabilizing frame designed to allow the urination assistance device to rest upon a toilet seat or upon the rim of the toilet bowl;
   the stabilizing frame further comprising a cross member connected to a base member, the receptacle operably connected through the base member at the outer wall of the front of the toilet;
   the cross member further defines a pair of ends, with each end terminating with a downward oriented elbow; and
   the base member including a downward directed spout in operative communication with the receptacle to discharge any urine collected within the receptacle into the toilet bowl, the spout being in or in near contact with the upper portion of the interior wall of the front of the toilet bowl.

2. The urination assistance device of claim 1, wherein the receptacle is generally funnel-shaped to assist downward movement of the urine within the receptacle, and acts as a splash guard to prevent urine from splashing and spilling around the toilet.

3. The urination assistance device of claim 2, wherein the lower surface wall of the receptacle extends further away from an opening defined in the bottom of the receptacle, to provide a larger surface for catching urine to further prevent splashing and spilling of the urine.

4. The urination assistance device of claim 1, wherein the receptacle includes an outlet leg operably connected to the stabilizing frame, the outer leg extending downwardly toward the toilet bowl to discharge urine collected within the receptacle.

5. The urination assistance device of claim 4, wherein the outer leg includes a telescopic extendable member that allows the length of the outer leg to be increased or decreased.

6. The urination assistance device of claim 4, wherein the lower portion of the outlet leg includes a flexible, ribbed or corrugated tube portion capable of being stretched or bent.

7. The urination assistance device of claim 4, wherein the terminus of the outer leg defines a downward directed nub, the nub being in or in near contact with an outer wall of a toilet bowl rim or seat when the urination assistance device is in use, the nub serving as one of the stabilizing components of the stabilizing frame.

8. The urination assistance device of claim 1, wherein the terminus of the receptacle defines a downward directed nub, the nub being in or in near contact with an outer wall of a toilet bowl rim or seat when the urination assistance device is in use, the nub serving as one of the stabilizing components of the stabilizing frame.

9. The urination assistance device of claim 7, wherein the nub and the spout are spaced sufficiently apart to allow a toilet seat and rim of a conventional width to fit between the nub and the spout, the nub and spout generally preventing the urination assistance device from moving away and toward the toilet bowl.

10. The urination assistance device of claim 1, wherein the base member is removably attached to the cross member.

11. The urination assistance device of claim 1, wherein the base member defines a barrier on the opposite side of the location of the spout.

12. The urination assistance device of claim 11, wherein the portion of the base member past the spout is solid.

13. The urination assistance device of claim 1, wherein the end comprises a telescopic extendable member to allow the length of the end to be increased or decreased.

14. The urination assistance device of claim 1, wherein the elbow is weighted.

15. The urination assistance device of claim 14, wherein the elbow is manufactured with a material heavier than the remaining components of the urination assistance device.

16. The urination assistance device of claim 1, wherein the base member extends past the widest portion of the toilet bowl, so that when extended to the desired length, the length of the cross member is less than the diameter of the toilet bowl.

17. A urination assistance device for use with a bowl toilet comprising:
   a receptacle for collecting urine, the receptacle extending downwardly;
   a stabilizing frame designed to allow the urination assistance device to rest upon a toilet seat or upon the rim of the toilet bowl, the receptacle operably connected to the stabilizing frame by an outlet leg operably connected to the stabilizing frame, the outlet leg extending downwardly toward the toilet bowl to discharge urine collected within the receptacle at the outer wall of the front of the toilet;

the stabilizing frame further comprising a pair of ends connected by a telescopic extendable member to allow the length between the ends to be increased or decreased;

each end terminating with a downward oriented weighted elbow; and the stabilizing frame including a downward directed spout in operative communication with the receptacle to discharge any urine collected within the receptacle into the toilet bowl, the spout being in or in near contact with the upper portion of the interior wall of the front of the toilet bowl.

18. The urination assistance device of claim 17, wherein the stabilizing frame further comprises a cross member connected to a base member, the receptacle operably connected through the base member at the outer wall of the front of the toilet, the cross member further defining the ends.

19. The urination assistance device of claim 17, wherein the elbow is manufactured with a material heavier than the remaining components of the urination assistance device.

* * * * *